United States Patent [19]

Greenberg

[11] Patent Number: 4,828,559
[45] Date of Patent: May 9, 1989

[54] BREAST FORM

[76] Inventor: Bert Greenberg, 1201 S. Ocean Dr., Hollywood, Fla. 33019

[21] Appl. No.: 135,725

[22] Filed: Dec. 21, 1987

[51] Int. Cl.[4] .............................................. A61F 2/12
[52] U.S. Cl. .......................................... 623/7; 450/57
[58] Field of Search ................... 623/7, 8; 450/54, 55, 450/56, 57

[56] References Cited

U.S. PATENT DOCUMENTS

| 2,542,619 | 2/1951 | Bernhardt | 623/7 |
| 2,851,692 | 9/1958 | Livingston et al. | 623/7 X |
| 3,304,558 | 2/1967 | Mann | 450/57 X |
| 3,514,792 | 9/1968 | Freedman | 623/7 |
| 3,811,133 | 5/1974 | Harris | 623/7 |
| 4,071,914 | 2/1978 | Silverman | 623/7 |
| 4,701,230 | 10/1987 | Loi | 623/7 X |

FOREIGN PATENT DOCUMENTS 2457041  6/1976  Fed. Rep. of Germany .......... 623/7

*Primary Examiner*—Richard J. Apley
*Assistant Examiner*—Alan W. Cannon
*Attorney, Agent, or Firm*—McAulay, Fields, Fisher, Goldstein & Nissen

[57] ABSTRACT

The present invention provides a breast form that is adapted to be located within a pocket formed by a cover flap connected to the cup of a brassiere. In a preferred embodiment the breast form includes a body member having an outer protruding surface that terminates in a base edge that is configured to fit against the juncture of the cup and the cover flap. The body member has a chamber that is spaced from the base edge. A weighted member, located within this chamber, is thus also spaced from the base edge to produce a moment in the brassiere cup that is resolved as a tensile force in a strap of the brassiere. The wearer experiences this tensile force as that produced by a breast form, located within the cup of the brassiere, that weighs more than the combined weight of the body member and the weighted member. As a result, a breast form in accordance with the present invention can be made much lighter than breast forms of the prior art while still giving the wearer the sensation of a weight in the brassiere strap that approximates a missing breast.

4 Claims, 1 Drawing Sheet

BREAST FORM

FIELD OF THE INVENTION

The present invention relates to breast forms that are worn within the cup of a brassiere as a prothesis after surgery for removal of a breast.

BACKGROUND OF THE INVENTION

As can be appreciated, a patient suffers severe physiological and psychological trauma following surgery for removal of a breast. During the recovery period, patients complain of a feeling of physical imbalance. Such feelings of imbalance can be so severe that the patient is unable to walk without falling. At the very least, patients tend to hunch their shoulders towards the site of the surgery. These feelings of imbalance persist even after the patient has fully recovered from the surgery. The psychological trauma experienced after such surgery always remains with such patients. This trauma is reinforced on a daily basis when the patient dresses and views the site of the missing breast and the unattractive scar that can result from such surgery.

In order to alleviate the post-operative trauma that results from the removal of a breast, the prior art has provided breast forms that fit within a sewn pocket that is formed within the cup of a brassiere. Some breast forms of the prior art are fabricated from a silicone gel that is encapsulated in a polyethlene coating that is adhered to the gel. In order to alleviate the patient's sensation of imbalance, such breast forms are sized with a uniformly distributed weight to approximately simulate the weight of the missing breast. In this regard, for a given cup size of a brassiere, the breast form weighs slightly less than an average breast because the breast in a brassiere cup is partially supported by the chest of a patient. Even so, such breast forms can weigh 14 ounces. Thus, when the patient dresses in the morning and inserts a breast form into a pocket of a brassiere, the psychological trauma due to such surgery is reinforced because the wearer is confronted with the thought of her missing breast when handling the weighted breast form.

The present invention provides a breast form that acts to restore a wearer's sense of balance after breast surgery while having a lighter weight than breast forms of the prior art. Moreover, the pocket containing the breast form of the present invention is preferably sewn so that the breast form is permanently attached to the brassiere and the breast form is never handled by the wearer. The lighter weight of the breast form of the present invention alleviates the traumatic, reinforcing act of a wearer sensing the weight of the breast form. This is accomplished in the present invention by providing a breast form that has a concentrated weight instead of the uniformly distributed weight of the breast forms of the prior art. The concentrated weight, as viewed when the breast form is located within the brassiere cup, is located so as to be spaced from the chest wall. The weight being spaced from the chest wall is thereby leveraged to induce a moment which is resolved as a tensile force in the brassiere strap. The importance of this is that the wearer senses the weight of any breast form by the loading on the brassiere strap. The leveraging of the weight in the breast form of the present invention results in a tensile force that is equivalent to a tensile force produced by a prior art breast form of heavier weight. Although one would expect a heavier breast form of the prior art to produce a greater loading in the brassiere strap, the concentrated weight in the breast form of the present invention and the spacing thereof from the wearer's chest is selected to be approximately equal to the tensile forces produced in the brassiere strap by a prior art breast form. The reason for this relates to the fact that all breast forms, as viewed when the breast form is located within the brassiere cup, rapidly narrow from the chest wall to the end of the brassiere cup. As such, since the weight of a prior art breast form is uniformly distributed throughout, the center of gravity of a prior art breast form is located towards the chest wall and hence, is relatively unleveraged. Thus, the weight is supported by the panels of the brassiere that support the cup, rather than by the brassiere strap. The wearer does not sense the weight of the breast form by the loading on the panels, but, as stated previously, by the tension and loading on the brassiere strap.

SUMMARY OF THE INVENTION

The present invention provides a breast form that is adapted to be located within a pocket formed by a cover flap connected to the cup of a brassiere. In a basic form, the present invention comprises a body member and a weighted member located within the body member. The body member includes a protruding, curved end surface that is contoured to simulate the outer surface of a breast located within the cup. The end surface has an apex of curvature from which the end surface outwardly and radially curves. A base surface, spaced from the apex of curvature, is provided to bear against the cover flap and the chest of a wearer. An outer base edge is provided, spaced from the apex of curvature, that is configured to fit within the juncture of the cup and the cover flap, adjacent to the chest of a wearer. The outer base edge connects the base surface to the end surface. The body member also includes a chamber, located between the apex of curvature and the base edge, so as to be spaced from the base edge and surrounded by the end surface. A weighted member is located within this chamber and is thus also spaced from the base edge. As a result, a moment is generated by the weighted member, within the cup, that is resolved as a tensile force on a brassiere strap which the wearer senses as a breast form having a greater weight than the combined weight of the body member and the weighted member of the breast form of the present invention. As a result, a breast form in accordance with the present invention can be made much lighter than breast forms of the prior art while still giving the wearer the sensation of a weight in the brassiere straps that approximate a missing breast. In this regard, a breast form made in accordance with the present invention can weigh 5 ounces as compared with a 14 ounce equivalent breast form of the prior art thereby effecting a savings of approximately 35% by weight of the present breast form over breast forms of the prior art.

DETAILED DESCRIPTION

Figure 1:
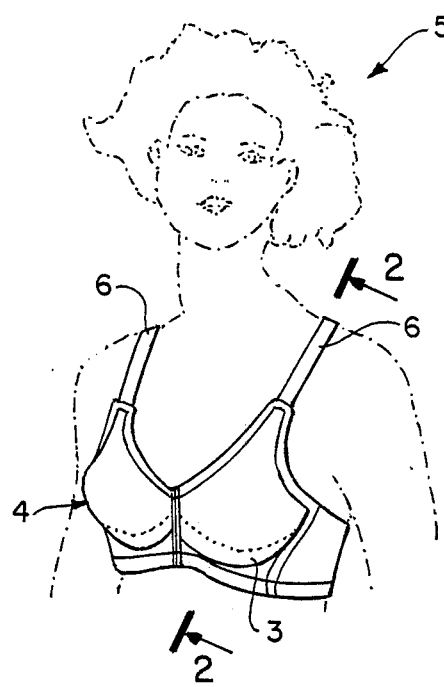
FIG. 1 is a perspective view of a brassiere incorporating the breast form of the present invention worn on a wearer illustrated by phantom lines.

With reference to the drawings, the present invention can include a breast form 1 that is adapted to be located within a pocket formed by a cover flap 2 connected to a cup portion 3 of a brassiere 4 worn on a wearer 5. Breast form 1 is preferably fabricated from polyurethane foam to simulate the resiliency of a natural breast. The breast form 1 includes a body member 10 preferably having a vaulted endwall 11 to provide a protruding, curved end surface 12. Surface 12 is contoured to simulate the outer surface of a normal breast. The end surface 12 has an apex of curvature, represented by 14, from which the end surface 12 outwardly and radially curves. An outer base edge, represented by 16, that is spaced from the apex 14, connects base surface 17 to the end surface 12. The base edge 16 is configured to fit within the juncture of the cup 3 nd the cover flap 2. The base surface 17, that is also spaced from apex 14, is configured to bear against cover flap 2 and thus against the chest of the wearer 5.

The body member 10 also has a chamber 36 that is located between the apex 14 and the base edge 16 so as to be spaced from the base edge 16 and surrounded by end surface 12. A weighted member 40 is located within the chamber 36 and is therefore, also spaced from the base edge 16. As a result, a moment is induced in the brassiere cup 3 which is resolved as a tensile force, indicated by arrow A, on a brassiere strap 6 that the wearer senses as a breast form located within the cup 3 that has a greater weight than the body member 10 and the weighted member 40. As previously mentioned, the spacing and the actual weight of weighted member 40 is selected to simulate the sensation of weight that a wearer experiences with heavier breast forms of the prior art.

For reasons that have been stated above, most of the mass of a breast form of the prior art would be concentrated towards the base edge 16. In contrast, the mass of the breast form 1 is closer to the apex 14. Thus, although a breast form 1 constructed in accordance with the present invention can be made with a lighter weight than a breast form of the prior art, the weight is leveraged to provide a tensile force in the brassiere strap 6 that is equivalent to the tensile force of a heavier, prior art breast form.

Figure 2:
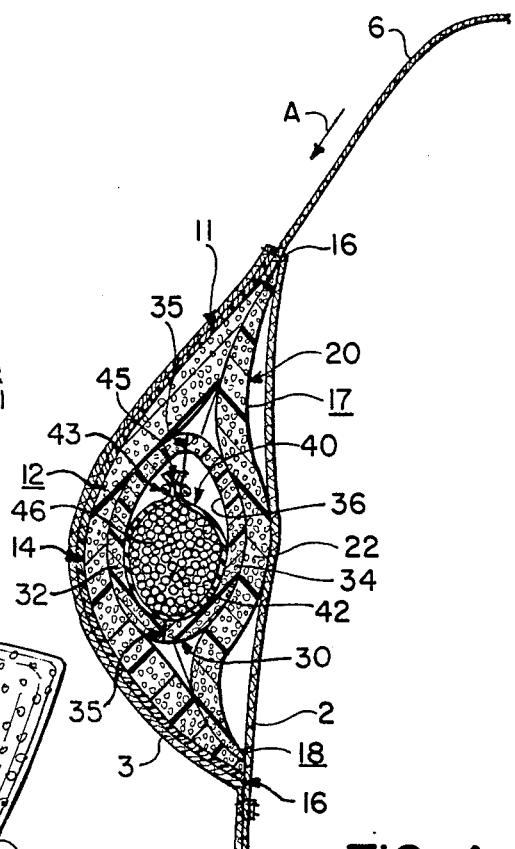
FIG. 2 is a cross-sectional view taken along lines 2—2 of FIG. 1.
Figure 3:
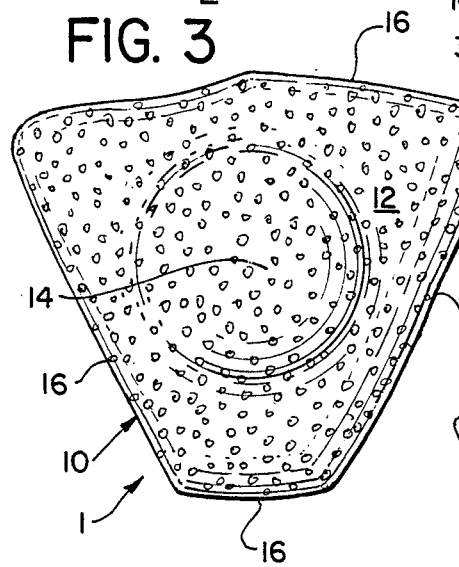
FIG. 3 is a top plan view of a breast form of the present invention.
Figure 4:
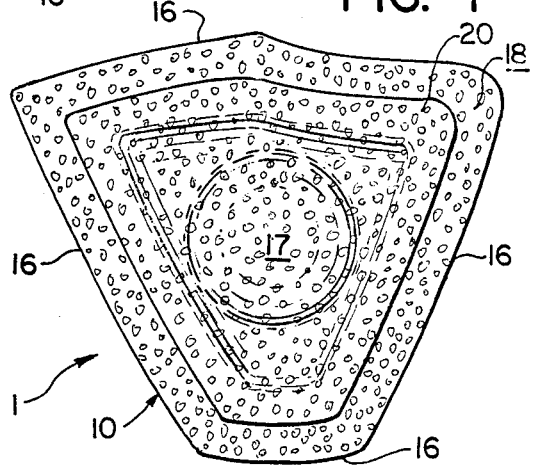
FIG. 4 is a bottom plan view of a breast form of the present invention.

Having briefly described the preferred embodiment, a more detailed description begins with a description of the vaulted endwall 11. With reference now to FIGS. 2 and 3, the endwall 11 terminates, at one end, in the apex of curvature 14 and terminates, at the other end, in an annular surface 18, the outer edge of which forms the base edge 16. The exterior surface of the endwall 11 forms the end surface 12. In the preferred embodiment, a basewall 20 can be connected to the endwall 11 within the annular surface 18. In the preferred embodiment, the base surface 17 is formed by the annular surface 18 and the basewall 20. The basewall 20 is preferably recessed towards the apex of curvature, illustrated by 14, so that the breast form 1 can accomodate a variety of types of surgery. For reasons that will become apparent, the base wall 20 also preferably has a centrally located dimple 22 that is oriented away from the apex of curvature, illustrated by 14.

With reference now to FIG. 2, a flattened hollow sphere 30 is provided to form the chamber 36 by incapsulating the weighted member 40. The hollow sphere can preferably be formed in a pair of hemispheres 32 and 34 that are joined together at 35. The hemispheres of 32 and 34 can preferably be respectively connected to the endwall 11 and the basewall 20 at the dimple 22. The dimple 22 supports the weighted member 40 to provide a cushion between the weighted member 40 and the chest of the wearer.

The weighted member 40 is preferably formed from a distensible orbicular element 42 that is sealed by a knot 43 tied around an opening 45 thereof. The element 42 is filled with a plurality of weighted pellet-like elements 46. When forces are applied to deform the body member 10, the weighted member 40 also deforms to retain the resiliency of the breast form. In this regard, element 42 can be formed from rubber, a thin plastic sheet and the like; and element 46 can be lead shot.

As can be appreciated by those skilled in the art, the preferred embodiment of the present invention, illustrated herein, is preferably formed from the inside out. The element 40 is first sized and filled with a sufficient number of pellet-like elements 46 through opening 45 for the given size of the breast form 1 and the brassiere cup 3. The element 42 is then sealed by a knot 43. The assembled weighted member 40 is then placed within the hemispheres 32 and 34 of the sphere 30. The hemispheres 32 and 34 are then joined at 35 by an adhesive. An adhesive is then applied to respectively join the hemispheres 32 and 34 to the basewall 20 and the endwall 10. The adhesive used in connecting the members together is preferably an acrylic cold adhesive.

While specific embodiments have been shown, the invention should not be considered as so limited, but only as so limited as set forth in the appended claims.

I claim:

1. An improved breast form adapted to be located within a pocket formed by a cover flap connected to the cup of a brassiere, said breast form comprising:
   an endwall contoured to simulate the outer surface of a breast, said endwall having an apex of curvature;
   a basewall spaced from said endwall and configured to bear against the cover flap, said curved endwall and said basewall being connected along a peripheral base edge;
   a chamber positioned between said apex of curvature and said basewall, said chamber being substantially spaced from said basewall and substantially spaced from said base edge; and
   a concentrated pre-determined weight located within said chamber and substantially spaced from said basewall to produce a moment in the cup that is resolved as a tensile force in a strap of the brassiere;
   said concentrated weight comprising a distensible scaled element and a plurality of weighted pellet-like elements filling said distensible element, said concentrated weight deforming in response to pressure thereon, by virtue of said pellets moving relative to one another and said element distending to accommodate such movement;
   said concentrated weight being positioned to provide a tension in said strap equal to that provided by a uniformly weighted breast form having at least twice the weight of said improved breast form.

2. The breast form improvement of claim 1 wherein said endwall and said basewall are formed from resilient material to provide cushioning between said concentrated weight and the surfaces of said breast form.

3. The breast form improvement of claim 1 wherein said basewall has a centrally located dimple having a curvature opposite to the curvature of said apex.

4. The breast form improvement of claim 2 wherein said basewall has a centrally located dimple having a curvature opposite to the curvature of said apex.

* * * * *